United States Patent [19]
Cordes et al.

[11] Patent Number: 5,985,311
[45] Date of Patent: Nov. 16, 1999

[54] TRANSDERMAL HORMONE PATCH

[75] Inventors: Guenter Cordes, Leichlingen; Martin Siegmund, Leverkusen, both of Germany

[73] Assignee: Labtec Gesellschaft fuer techologische Forschung und Entwicklung mbH, Langenfeld, Germany

[21] Appl. No.: 09/010,534

[22] Filed: Jan. 22, 1998

Related U.S. Application Data

[63] Continuation-in-part of application No. PCT/EP96/03229, Jul. 22, 1996.

[51] Int. Cl.$^6$ .................................................. A61F 13/02
[52] U.S. Cl. ........................... 424/428; 514/946; 514/947
[58] Field of Search ............................ 424/448; 514/946, 514/947

[56] References Cited

U.S. PATENT DOCUMENTS

| | | |
|---|---|---|
| 4,913,905 | 4/1990 | Fankhauser et al. . |
| 5,053,227 | 10/1991 | Chiang ..................................... 424/448 |
| 5,194,455 | 3/1993 | Massow . |
| 5,223,261 | 6/1993 | Nelson et al. . |
| 5,296,230 | 3/1994 | Chien et al. . |
| 5,306,503 | 4/1994 | Muller et al. . |
| 5,314,685 | 5/1994 | Tyle et al. . |
| 5,393,529 | 2/1995 | Hoffmann et al. . |
| 5,518,734 | 5/1996 | Stefano ..................................... 424/448 |
| 5,676,968 | 10/1997 | Lipp et al. . |
| 5,686,098 | 11/1997 | Murphy . |
| 5,711,962 | 1/1998 | Cordes et al. . |

FOREIGN PATENT DOCUMENTS

| | | |
|---|---|---|
| 371469 | 11/1989 | European Pat. Off. . |
| 399432 | 5/1990 | European Pat. Off. . |
| 416842 | 9/1990 | European Pat. Off. . |
| 38 10 896 | 10/1988 | Germany . |
| 39 10 578 | 10/1990 | Germany . |
| 39 42 232 | 6/1991 | Germany . |
| 39 33 460 | 3/1992 | Germany . |
| 42 10 165 | 2/1993 | Germany . |
| 40 20 144 | 7/1993 | Germany . |
| 43 09 830 | 5/1994 | Germany . |
| 43 33 595 | 4/1995 | Germany . |
| 42 41 874 | 3/1997 | Germany . |
| WO 93/08795 | 5/1993 | WIPO . |
| WO 93/10772 | 6/1993 | WIPO . |
| WO 94/15609 | 7/1994 | WIPO . |
| WO 95/02404 | 1/1995 | WIPO . |
| WO 95/05137 | 2/1995 | WIPO . |
| WO 95/20392 | 8/1995 | WIPO . |
| WO 96/08229 | 3/1996 | WIPO . |
| WO 96/08255 | 3/1996 | WIPO . |

OTHER PUBLICATIONS

Franz, "Percutaneous Absorption on the Relevance of In Vitro Data", *The Journal of Investigate Dermatology*, 64:190–195 (1975).

Katz et al., "Enhanced skin Permeation of Prazosin by Transcutol–Oleic Acid Mixture", *Proceed. Intern. Symp. Control. Rel. of Bioact. Mater.*, 18: 533–534 (1991).

Frieg–Falson et al., "Characterization of the Enhancing Effect of a Vehicle in a Transdermal System", *Drug Development and Industrial Pharmacy*, 15(14–16), 2393–2406 (1989).

Watkinson et al., "Aspects of the Transdermal Delivery of Prostaglandins", *International Journal of Pharmaceutics*, 74 (1991) 229–256.

Walters et al., "Penetration Enhancers and Their Use in Transdermal Therapeutic Systems", *Transdermal Drug Delivery: Developmental Issues and Research Initiatives*, edited by Hadgraft and Guy, Marcel Dekker, Inc., 1989, pp.

(List continued on next page.)

*Primary Examiner*—D. Gabrielle Brouillette
*Attorney, Agent, or Firm*—Kane, Dalsimer, Sullivan, Kurucz, Levy, Eisele and Richard, LLP

[57] ABSTRACT

A transdermal therapeutic system (TTS) which contains as the active ingredients an oestrogen and a gestagen or a gestagen or androgen as well as an acrylate adhesive and, as resorption promoters, the two substances oleic acid and 2-(2-ethoxyethoxy)ethanol.

8 Claims, 1 Drawing Sheet

Penetration of a gestagen from a TTS through stratum corneum in a Franz cell

OTHER PUBLICATIONS

Abstract of Katz et al., "Enhanced Skin Permeation of Prazosin by Transutol–oleic Acid Mixture", *Proc. Program. Int. Symp. Controlled Release Bioact. Mater.*, 18$^{th}$ (1991) 533–544.

Abstract of Rieg–Falson et al., "Evaluation of a Transdermal Device Containing Testosterone", *Bull. Tech./Gattefosse Rep.*, 78: 89–96 (1985).

Abstract of Published Canadian Patent Application No. CA 2,012,875 (1990).

TRANSDERMAL HORMONE PATCH

CROSS-REFERENCE TO RELATED APPLICATIONS

This application is a continuation-in-part of co-pending International Patent Application No. PCT/EP96/03229, filed Jul. 22, 1996 designating the United States, which in turn claims convention priority of German Patent Application No. DE 195 26 864.4, filed Jul. 22, 1995.

FIELD OF THE INVENTION

The present invention relates to a patch to be applied to the skin, which is also termed a transdermal therapeutic system (TTS), in which up to three drug substances are contained which are released from the TTS, through the skin, into the body (systemic circulation) of the human or of the animal. The dermal patch comprises a backing film and a pressure-sensitive adhesive in which the drug substances as well as other substances, for example resorption accelerators, are situated. In addition, a further adhesive layer is optionally provided, as is a protective film, which is removed by pulling it off before the patch is used.

BACKGROUND OF THE INVENTION

Dermal patches for the transdermal administration of drug substances are known. One problem with these preparations is the resorption of sufficiently large amounts of active ingredient per unit area and per unit time, because many drug substances which are deposited on or stuck on to the skin in a topical preparation do not pass through the skin in sufficient amounts.

For this reason, so-called resorption accelerators, which are also termed penetration improvers, resorption promoters or enhancers, have been investigated and have been incorporated in dermal patches. In this manner, it has often been possible to achieve the desired pharmacological effect for the first time. Examples of resorption accelerators include propylene glycol, polyethylene glycols of lower molecular weight, oleic acid, isopropyl myristate, myristol, "Gattefosse" Transcutol, "Henkel" Eutanol, glycerol monolaurate (="Huls" Imvitor 312), a partial glyceride of ricinoleic acid (="Huls" Softigen 701), unsaturated polyglycolized glycerides (="Gattefosse" Labrafil M1944CS), "Gattefosse" Labrafac Hydro WL1219, Estasan GT60. saturated polyglycolized glycerides (="Gattefosse" Labrasol), phospholipids, etc. Further literature thereon: Rieg-Falson, F. et al. 1989, Watkinson, A. C. et al. 1991, and Hadgraft, J. and Guy. R. H. (eds.): Marcel Dekker Inc. N.Y. 1989.

A transdermal therapeutic system (TTS) having a backing film and having an acrylate-based pressure-sensitive adhesive, having a hormone content and a content of a plurality of resorption accelerators, is already known from WO-A-96/08 255, wherein
the hormone content is provided by a content of levonorgestrel, and
the resorption accelerators may comprise, amongst others, a $C_{8-22}$ fatty acid such as oleic acid (page 6, line 25), or 2-(2-ethoxyethoxy)-ethanol, a mixture of oleic acid and 2-(2-ethoxyethoxy)-ethanol per se is not mentioned.

Acrylate-based pressure-sensitive adhesives form part of the prior art, such as those based on DUROTAK™, for example, which are obtainable by the radical polymerization of butyl acrylate, 2-ethylhexyl acrylate, methylacrylate, vinyl acetate, acrylic acid and/or hydroxyethyl acrylate; see the list of monomers for DUROTAK™280-2287, for example.

SUMMARY OF THE INVENTION

In contrast to this prior art, the present invention relates to a transdermal therapeutic system (TTS) transdermal therapeutic system (TTS) having a backing film, having an acrylate-based pressure-sensitive adhesive, having a hormone content and a content of resorption accelerators and having a protective film, wherein
the hormone content is provided by a content of oestrogen and/or gestagen and/or androgen, and
the resorption accelerators are the two substances oleic acid and 2-(2-ethoxyethoxy)ethanol.

The present invention therefore relates to a patch to be applied to the skin, which is also termed a transdermal therapeutic system (TTS), in which up to three drug substances are contained which are released from the TTS, through the skin, into the body (systemic circulation) of the human or of the animal. The dermal patch comprises a backing film and a pressure-sensitive adhesive in which the drug substances as well as other substances, for example resorption accelerators, are situated. In addition, a further adhesive layer is optionally provided, as is a protective film, which is removed by pulling it off before the patch is used.

Therefore, this invention also relates to the use of a mixture of the two substances oleic acid and 2-(2-ethoxyethoxy)ethanol jointly in a TTS as enhancers for oestrogens such as oestradiol and ethinyl oestradiol, gestagens such as norethisterone acetate, levonorgestrel or chlormadinone acetate and/or androgens such as testosterone.

Moreover, it should also be emphasized as being advantageous that these are two known substances, which are customary and harmless as adjuvant substances in pharmaceutical preparations, and are not new chemical substances which would involve the risk of side-effects and would have to be tested in long-term toxicological investigations before they could be employed in a medicine for human use.

This invention further relates to a transdermal therapeutic system which is characterized in that the oestrogen can be oestradiol or ethinyl oestradiol and the gestagen can be norethisterone acetate, levonorgestrel, progesterone or chlormadinone acetate, and the androgen can be testosterone, wherein these hormones can also be used in the form of other salts or esters, or of the bases also.

The transdermal therapeutic system according to the invention may be characterized in that the acrylate-based pressure-sensitive adhesive is obtained by the radical polymerization of butyl acrylate, 2-ethylhexyl acrylate, methacrylate, vinyl acetate, acrylic acid, hydroxyethyl acrylate or from mixtures of some or all of the cited monomers, and/or that cross-linking agents and/or other adjuvant substances have been added in an amount less than 2%.

The transdermal therapeutic system according to the invention may further be characterized in that the ratio by weight of oleic acid to 2-(2-ethoxyethoxy)-ethanol is 2:1 to 1:2, preferably 1.5:1 to 1:1.5, and the amount of this mixture is 1 to 10 percent by weight with respect to the TTS weight, including all the active ingredients and adjuvant substances, but not including the films such as the backing film and the release liner.

The transdermal therapeutic system according to the invention may further be characterized in that it contains oestradiol and norethisterone acetate, or oestradiol and levonorgestrel, or ethinyl oestradiol and levonorgestrel, or testosterone.

BRIEF DESCRIPTION OF THE DRAWINGS

The accompanying

DESCRIPTION OF PREFERRED EMBODIMENTS

Figure 1:
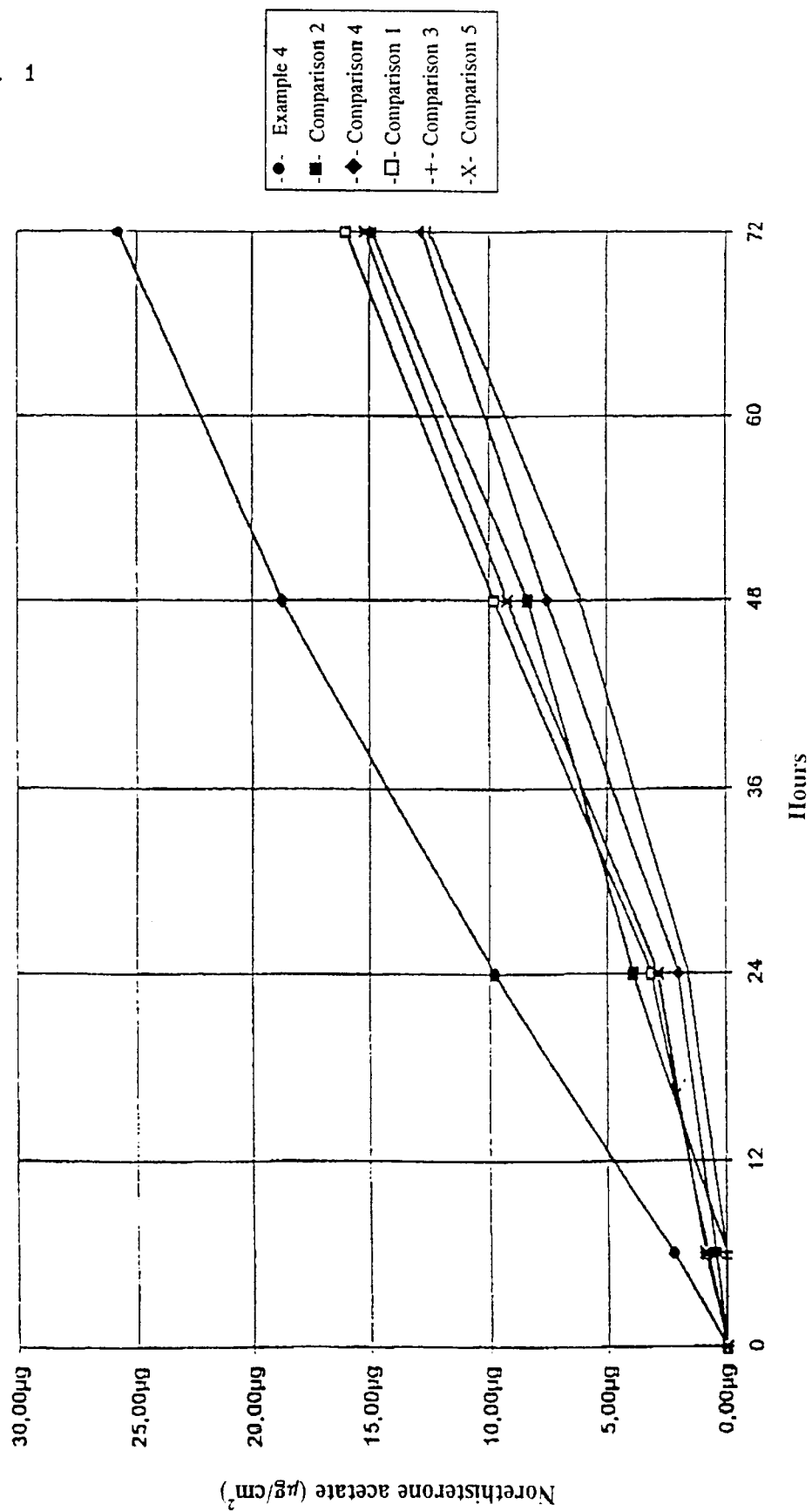
FIG. 1 is a graph showing the penetration of a gestagen from a transdermal treatment system through stratum corneum in a Franz cell over time of a test composition according to the present invention and several comparison compositions.

In the context of our work on the development of dermal patches comprising different drug substances, a very large number of penetration improvers has been incorporated in the formulation, and the release of the active ingredient has been investigated. The latter has been tested in the USP paddle apparatus (described in United States Pharmacopoeia XXIII), penetration through "hairless mouse skin" has been tested using the Franz cell model (Franz cell: Franz, T. J., J. Invest. Dermatol. 1975 (64), pages 191–195), and penetration through human stratum corneum has likewise been tested in the Franz cell. The penetration-promoting substances comprised oleic acid DAB 10, 2-(2-ethoxyethoxy)ethanol, Eutanol G (DAB 10), Labrafac and Labrafil, as well as mixtures comprising oleic acid/2-(2-ethoxyethoxy)ethanol, oleic acid/Labrafil, and oleic acid/Labrafac, in a ratio of approximately 1:1.

The release of active ingredient with time in the USP paddle apparatus exhibited no great differences.

On measuring the permeation through animal skin, and particularly through human stratum corneum, however, it was shown that dermal patches which were produced with a mixture of oleic acid and 2-(2-ethoxyethoxy)ethanol in a ratio of approximately 1:1 as enhancers gave significantly higher permeation rates than those which were observed on the addition of the individual enhancers or without enhancers. It was surprising that the mixture of oleic acid and 2-(2-ethoxyethoxy)ethanol gave permeation rates which were higher than those obtained when using mixtures of oleic acid and other enhancers. The former mixture is obviously distinguished by its special resorption-accelerating properties.

Examples are given below of the manner in which dermal patches according to this Patent Application, and comparison patches can be produced. Furthermore, the results on release of active ingredient and the results of permeation tests are described. An HPLC method such as that which is familiar to one skilled in the art was employed for the analysis of the active ingredient content in the acceptor medium.

EXAMPLE 1

In order to produce 1000 patches, the yield of which will be reduced as a result of coating and punching-out losses, 2.9 g oestradiol, micronized, and
3.5 g levonorgestrel were dissolved or very finely distributed, with stirring, in 330.0 g methyl ethyl ketone (MEK). Stirring was effected by means of a magnetic stirrer at about 25° C. in a glass vessel, with protection from light. The following were added with further stirring:

5.5 g oleic acid and
5.5 g 2-(2-ethoxyethoxy)ethanol, and also, after about 5 minutes
74.1 g of the commercially available 51% solution of the acrylate copolymer "Durotak 280-2287" manufactured by National Starch Chemical B. V., Zutphen, NL. and
409.5 g of the commercially available 37% solution of the acrylate copolymer "Durotak 326-1753" manufactured by the same company.

The mixture was stirred until a homogeneous phase was formed. The solution was subsequently spread on to a commercially available siliconized polyester film with a thickness of about 100 μm, in a customary apparatus intended for the production of patches, in an amount which gives a weight of film per unit area of about 70 mg per cm$^2$ after drying. The solvent of the film was caused to evaporate by heating the coated film to 40° C. for about 1 hour. An analysis of the residual solvent content was performed to check whether the drying time and temperature were sufficient. The temperature can be increased if necessary.

After drying, the adhesive side was covered with a polyester film having a thickness of 15 μm, and patches 30 cm$^2$ in size were thereafter punched out. Apart from the films, each patch had a content of 2.9 mg oestradiol
3.5 mg levonorgestrel
5.5 mg 2-(2-ethoxyethoxy)ethanol
5.5 mg oleic acid
37.8 mg Durotak 280-2287 solid matter
151.5 mg Durotak 326-1753 solid matter.

If necessary for medical application, patches with other surface areas can also be punched out, such as 20, 30 or 40 cm$^2$ for example. The amounts of active ingredient per TTS can be varied correspondingly.

The punched-out patches were packaged and sealed in the usual manner in suitable sealed bags.

EXAMPLE 2

In order to produce 1000 TTS patches (the yield will be less, as described in Example 1), the following substances were weighed into a glass vessel and stirred until homogeneity was reached, whilst protecting them from light:

30 g norethisterone acetate, micronized
5 g oestradiol, micronized,
420 g methyl ethyl ketone
8 g oleic acid
8 g 2-(2-ethoxyethoxy)ethanol
924 g Durotak 280-1753 as a commercially available 33% solution.

The subsequent procedure was as described in Example 1. Patches having a surface area 35 cm$^2$ (or of any other desired size) were punched out and packaged as described.

Without taking into account the backing film and the release liner, 1 cm$^2$ of a TTS produced in this manner has the following composition:

0.143 mg oestradiol
0.857 mg norethisterone acetate
0.229 mg oleic acid
0.229 mg 2-(2-ethoxyethoxy)ethanol
8.71 mg Durotak 280-1753 solid matter

EXAMPLE 3

In order to produce 1000 TTS patches (the yield is less, as stated above), the following substances were weighed into a glass vessel and stirred at room temperature until homogeneity was reached, whilst protecting them from light:

5.5 g oestradiol, micronized,
30 g chlormadinone acetate, micronized 5 g oleic acid
5 g 2-(2-ethoxyethoxy)ethanol
440 g methyl ethyl ketone
614 g Durotak 901-1052 as a commercially available 48% solution.

The procedure was otherwise as described in Example 1. Patches having a surface area of 35 cm² (or of any other desired size) were punched out and packaged. A 35 cm² TTS then has the following composition (without taking into account the backing film and the release liner):

5.5 mg oestradiol
30 mg chlormadinone acetate
5 mg oleic acid
5 mg 2-(2-ethoxyethoxy)ethanol
295 mg Durotak 901-1052 solid matter.

EXAMPLE 4

In order to produce 1000 TTS patches (see above for the loss in yield), the following substances were weighed into a glass vessel and stirred at about 25° C. until homogeneity was reached, whilst protecting them from light:

5.4 g oestradiol, micronized
35 g norethisterone acetate, micronized
10 g oleic acid
10 g 2-(2-ethoxyethoxy)ethanol
480 g methyl ethyl ketone
142 g Durotak 280-2287, commercially available 51% dilution
784 g Durotak 326-1753, commercially available 37% dilution.

After a homogeneous mixture was obtained, which was achieved after stirring for about 60 minutes, the solution was deposited on a 100 μm siliconized film as described in Example 1, and the solvent was removed by heating the batch to about 40° C. (about 1–2 hours). TTS patches having a surface area 43 cm² were subsequently punched out and packaged. Other surface areas can also be punched out.
A TTS patch then has the following composition:

5.4 mg oestradiol
35 mg norethisterone acetate
10 mg oleic acid
10 mg 2-(2-ethoxyethoxy)ethanol
72.4 mg Durotak 280-2287 dry matter
290 mg Durotak 326-1753 dry matter.

Investigation of the effect of the enhancer mixture according to the invention on permeation.

Example 4 and Comparative Examples 1 to 5.

Specimens according to Example 4 were used for this investigation. For comparison therewith specimens were used which were not according to the invention, which were produced as given in Example 4, but without the substances oleic acid and 2-(2-ethoxyethoxy)ethanol or with the addition of other enhancers, as can be seen from Table 1. The investigation was performed in a model Franz cell (Franz, T. J., J. Invest. Dermatol. 1975 (64), pages 191–195) using human stratum corneum. Stratum corneum from human skin was obtained as material from operations and was prepared as described by Tiemessen, M., Harry, L. G. M. and Bodde, H. E. in Int. J. of Pharmacol. 1989. Analysis of the active substances in the acceptor medium was performed by HPLC methods which are known in the art. As can be seen from Table 1 and FIG. 1, the permeation through human stratum corneum was significantly increased by the joint addition of oleic acid and 2-(2-ethoxyethoxy)ethanol to the TTS patches, by comparison with TTS patches which did not contain these two substances.

TABLE 1

Effect of enhancers on the permeation of norethisterone acetate

| Time | Comparison 1 | Example 4 | Comparison 2 | Comparison 3 | Comparison 4 | Comparison 5 |
|---|---|---|---|---|---|---|
|  | 2.5% oleic acid 2.5% Labrafil | 2.5% oleic acid 2.5% ethoxyeth* | 5% oleic acid | without enhancers | 2.5% ethoxyeth* | 2.5% oleic acid 2.5% Labrasol |
|  | Amount of norethisterone acetate in the acceptor |  |  |  |  |  |
| 0 hrs | 0.00 μg | 0.00 μg | 0.00 μg | 0.00 μg | 0.00 μg | 0.00 μg |
| 6 hrs | 0.78 μg | 2.21 μg | 0.00 μg | 0.00 μg | 0.43 μg | 0.87 μg |
| 24 hrs | 3.12 μg | 9.80 μg | 3.90 μg | 1.56 μg | 1.98 μg | 2.84 μg |
| 48 hrs | 9.80 μg | 18.70 μg | 8.34 μg | 6.12 μg | 7.56 μg | 9.22 μg |
| 72 hrs | 15.98 μg | 25.80 μg | 14.90 μg | 12.45 μg | 12.78 μg | 15.20 μg |

*) ethoxyeth = 2-(2-ethoxyethoxy)ethanol

The foregoing description and examples have been set forth merely to illustrate the invention and are not intended to be limiting. Since modifications of the disclosed embodiments incorporating the spirit and substance of the invention may occur to persons skilled in the art, the invention should be construed to include everything within the scope of the appended claims and equivalents thereof.

What is claimed is:
1. A transdermal therapeutic system which comprises;
   A. a backing film;
   B. a coating on the backing film which comprises;
      (i) an acrylate-based pressure-sensitive adhesive;
      (ii) a hormone selected from the group consisting of oestrogen, androgen and gestagen; and
      (iii) a resorption accelerator comprising a mixture of oleic acid and 2-(2-ethoxyethoxy)-ethanol wherein the mixture has been incorporated in an amount of 1 to 10 percent by weight of the system excluding the weight of the backing film plus the weight of the releasable protective film, and wherein the oleic acid and 2-(2-ethoxyethoxy)-ethanol have been incorporated with a ratio by weight of 2:1 to 1:2; and

C. a releasable protective film over the coating.

2. A transdermal therapeutic system according to claim 1, wherein the oestrogen is selected from the group consisting of oestradiol and ethinyl oestradiol, the gestagen is selected from the group consisting of norethisterone acetate, levonorgestrel, progesterone and chlormadinone acetate, and the androgen is testosterone, said hormones being in the form of a base or their pharmaceutically acceptable salts and esters.

3. A transdermal therapeutic system according to claim 1 wherein the acrylate-based pressure-sensitive adhesive has been obtained by radical polymerization of a compound selected from the group consisting of butyl acrylate, 2-ethylhexyl acrylate, methylacrylate, vinyl acetate, acrylic acid, and hydroxyethyl acrylate.

4. A transdermal therapeutic system according to claim 3, wherein the oleic acid 2-(2-ethoxyethoxy) ethanol have been incorporated in a ratio of 1.5:1 to 1:1.5.

5. A transdermal therapeutic system according to claim 1, wherein the hormone selected is oestradiol and norethisterone acetate.

6. A transdermal therapeutic system according to claim 1, wherein the hormone selected is oestradiol and levonorgestrel.

7. A transdermal therapeutic system according to claim 1, wherein the hormone selected is ethinyl oestradiol and levonorgestrel.

8. A transdermal therapeutic system according to claim 1, wherein the androgen is testosterone.

\* \* \* \* \*